(12) United States Patent
Cormier (10) Patent No.: US 8,343,774 B2
(45) Date of Patent: Jan. 1, 2013

(54) CHROMATOGRAPHY-BASED MONITORING AND CONTROL OF MULTIPLE PROCESS STREAMS

(75) Inventor: Sylvain Cormier, Mendon, MA (US)

(73) Assignee: Waters Technologies Corporation, Milford, MA (US)

( * ) Notice: Subject to any disclaimer, the term of this patent is extended or adjusted under 35 U.S.C. 154(b) by 54 days.

(21) Appl. No.: 12/919,565

(22) PCT Filed: Feb. 25, 2009

(86) PCT No.: PCT/US2009/035047
§ 371 (c)(1),
(2), (4) Date: Oct. 12, 2010

(87) PCT Pub. No.: WO2009/111228
PCT Pub. Date: Sep. 11, 2009

(65) Prior Publication Data
US 2011/0020939 A1 Jan. 27, 2011

Related U.S. Application Data

(60) Provisional application No. 61/032,676, filed on Feb. 29, 2008.

(51) Int. Cl.
*G01N 33/15* (2006.01)
*G01N 30/02* (2006.01)

(52) U.S. Cl. ......... 436/180; 436/161; 422/68.1; 422/70; 422/537; 422/539; 210/198.2; 210/656; 73/61.52; 73/61.55; 73/61.56

(58) Field of Classification Search ............... 436/8, 43, 436/55, 161, 174, 177, 178, 180; 422/63, 422/67, 68.1, 69, 70, 501, 509, 510, 537, 422/538, 539; 210/198.2, 656; 73/61.52, 73/61.55, 61.56
See application file for complete search history.

(56) References Cited

U.S. PATENT DOCUMENTS
3,744,219 A 7/1973 Tindle et al.
(Continued)

FOREIGN PATENT DOCUMENTS
GB 1334431 10/1973
(Continued)

OTHER PUBLICATIONS

Zecevic, et al; Validation of a high-performance liquid chromatographic method for the simultaneous determination of tramadol and its impurities in oral drops as a pharmaceutical formulation; J. chromatogr. A 1119 (2006) 251-256.

*Primary Examiner* — Maureen Wallenhorst
(74) *Attorney, Agent, or Firm* — Waters Technologies Corp (57) ABSTRACT

An analytical apparatus includes a sample-injection valve, a sample pump, at least two sources of standards, and a selection valve. The sample-injection valve has an output port in fluid communication with a LC column, and an input port in fluid communication with a mobile-phase supply line. The at least two sources of standards are associated with at least two pharmaceutical compounds. The selection valve fluidically and selectably connects the sample pump to the at least two sources of standards, to the sample-injection valve, and to at least two pharmaceutical-manufacturing process lines associated with the at least two pharmaceutical compounds. A method for controlling a pharmaceutical manufacturing process includes switching the selection valve to alternately and repeatedly sample the at least two sources of standards and material flowing through the at least two pharmaceutical-manufacturing process lines.

9 Claims, 6 Drawing Sheets

U.S. PATENT DOCUMENTS

| | | |
|---|---|---|
| 3,757,583 A | 9/1973 | Ludewig, Jr. |
| 3,827,302 A | 8/1974 | Sato et al. |
| 3,897,213 A * | 7/1975 | Stevens et al. .................. 422/81 |
| 3,918,913 A | 11/1975 | Stevenson et al. |
| 3,923,460 A * | 12/1975 | Parrott et al. ................. 436/149 |
| 4,156,437 A | 5/1979 | Chivens et al. |
| 4,158,630 A | 6/1979 | Stearns |
| 4,177,677 A | 12/1979 | Ruzicka et al. |
| 4,242,909 A | 1/1981 | Gundelfinger |
| 4,601,211 A | 7/1986 | Whistler |
| 4,681,678 A | 7/1987 | Leaseburge et al. |
| 4,684,465 A | 8/1987 | Leaseburge et al. |
| 4,836,038 A | 6/1989 | Baldwyn |
| 4,840,074 A | 6/1989 | Jessop |
| 5,091,092 A | 2/1992 | Newhouse et al. |
| 5,107,908 A | 4/1992 | Newhouse et al. |
| 5,297,431 A | 3/1994 | White |
| 5,417,853 A | 5/1995 | Mizuno et al. |
| 5,922,106 A | 7/1999 | Mowry et al. |
| 6,294,388 B1 | 9/2001 | Petro |
| 6,382,035 B1 | 5/2002 | Nichols |
| 2004/0038384 A1 | 2/2004 | Dussauze et al. |
| 2004/0232080 A1 | 11/2004 | Neyer et al. |
| 2005/0037517 A1 | 2/2005 | Anderson et al. |
| 2005/0194318 A1 | 9/2005 | Ozbal et al. |
| 2006/0054543 A1 | 3/2006 | Petro et al. |
| 2006/0156792 A1 | 7/2006 | Wang |
| 2007/0277596 A1 | 12/2007 | Kim et al. |

FOREIGN PATENT DOCUMENTS

| | | |
|---|---|---|
| JP | 57-192863 | 11/1982 |
| JP | 2004168357 | 6/1992 |
| WO | 93/07168 | 5/1993 |

* cited by examiner

CHROMATOGRAPHY-BASED MONITORING AND CONTROL OF MULTIPLE PROCESS STREAMS

RELATED APPLICATIONS

The application claims priority to U.S. Provisional Patent Application No. 61/032,676, filed Feb. 29, 2008, the entire contents of which are incorporated herein by reference.

TECHNICAL FIELD

The invention relates to chromatographic apparatus and methods, and, in particular, to apparatus and methods that support monitoring and control of drug manufacturing processes.

BACKGROUND OF THE INVENTION

Liquid chromatography (LC) involves a separation process, which supports chemical analysis and preparation. A typical LC apparatus includes a tube or other vessel packed with a stationary inert porous material; a fluid containing a sample of interest is passed through the porous material. In a typical case, the stationary material includes particles.

More generally, a typical LC system includes a mobile-phase pump, a sample injector, a column, and a detector. The pump propels a mobile-phase fluid along a fluidic path that passes through the injector, column, and detector. The injector introduces a sample into the mobile-phase fluid prior to entry of the fluid into the column.

Typically, mobile-phase solvents are stored in reservoirs, and delivered as required via reciprocating-cylinder based pumps. Sample materials are often injected via syringe-type pumps. For example, some LC systems inject a sample by aspirating (pulling) a fluid-based sample into a tube via a needle or capillary and then pushing the sample into a sample loop. The sample is then injected from the sample loop into the mobile-phase stream on its way to a separation column.

Distinct chemical compounds contained in the fluid often have distinct affinities for the stationary material held in the column. Consequently, as the fluid moves through the chromatographic column, various chemical compounds are delayed in their transit through the column by varying amounts of time in response to their interaction with the stationary porous material in the column. As a result, as the compounds are carried through the medium, the compounds separate and elute from the column over different periods of time.

The different chemical compounds in a sample solution typically separate out as individual concentration peaks in the fluid eluting from the column. The various separated chemicals can be detected by, for example, a refractometer, an absorbtometer, or some other detecting device into which the fluid flows upon leaving the chromatographic column, such as a mass spectrometer.

LC has potential as a tool in support of Process Analytical Technology (PAT). PAT entails apparatus and methods that are employed in support of pharmaceutical manufacturing. A typical PAT system supports analysis and control of manufacturing through timely measurements (i.e., during processing) of critical quality and performance attributes of raw and in-process materials and processes with the goal of ensuring final product quality. The word "analytical", with respect to PAT tools, broadly relates to chemical, physical, microbiological, mathematical, and risk analysis conducted in an integrated manner.

In the PAT context, LC is used, for example, to determine when a desired reaction product, e.g., a drug, has begun to appear in a process stream, so that collection of the process stream may commence; LC is also used to determine when collection should cease. The effectiveness of LC analyses are limited, however, by the time delay between collection of a sample, and completion of analysis of the sample. This delay is related to the length of time required to collect a sample and the length of time required to analyze the sample. Analysis time alone can require, for example, a half hour to an hour, for some High-Performance LC (HPLC) equipment. Moreover, LC-based PAT equipment should be reliable and indicate an equipment fault as soon as possible after the fault occurs. Moreover, typical LC equipment does not readily lend itself to PAT support due to difficulty in interfacing the LC equipment to a compound-manufacturing process line.

The location of the output flow of a pharmaceutical-manufacturing process batch, in some cases, is directed through plumbing to accommodate the time lag exhibited by analytical data. After detection of the appearance of the desired compound in the process stream, collection can commence from an appropriate location of the plumbing. Limits in sampling frequency and in speed of sample collection and analysis limit the accuracy in optimal collection of the desired portion of a process stream. Such limits are costly.

SUMMARY

The invention arises, in part, from the realization that one LC apparatus can be configured to support multiple drug-manufacturing process streams through use of a source-selection component, where the source-selection component is plumbed to both the multiple process streams and to multiple standards sources associated with the pharmaceuticals being manufactured.

Preferred embodiments of the invention provide reduced sample-collection time lag, increased speed of analyses (on the order of minutes,) and greater frequency of analyses (e.g., data collected every five to ten minutes.) Such embodiments support process monitoring and start- and endpoint detection, and collection control. Moreover, the integrated monitoring of standards provides quick fault detection and response.

Accordingly, in one aspect, the invention features an analytical apparatus for monitoring and/or controlling multiple process streams in drug manufacturing. The analytical apparatus includes a injection valve, a sample pump, at least two sources of standards, and a selection valve.

The injection valve includes a sample loop, and has an output port in fluid communication with at least one chromatography separation column, such as an LC column, an input port in fluid communication with a solvent supply line, and two ports in fluid communication with the sample loop.

The selection valve has at least six ports. At least two of the ports are input ports in fluid communication with at least two pharmaceutical-manufacturing process lines; at least two of the ports are input ports in fluid communication with the at least two sources of standards; at least one of the ports is in fluid communication with the sample pump, and at least one of the ports is in fluid communication with a port of the sample-injection valve.

In another aspect, the invention features a method for controlling a pharmaceutical manufacturing process. The method includes provision of an apparatus, such as that described above, and switching the selection valve to alternately and repeatedly sample the at least two sources of standards and material flowing through the at least two pharmaceutical-manufacturing process lines.

The apparatus and method support drug manufacturing process monitoring and/or control with improved efficiency by permitting support of more than one process stream, rapid detection of apparatus errors, and automation of process monitoring and apparatus fault detection.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The term "in-line" herein refers to sample analysis of a process stream that occurs with little or no diversion of the process stream. For example, an in-line analysis optionally is accomplished by disposing a detector and/or related components in the flow path of a process stream.

The term "on-line" herein refers to sample analysis of a process stream that entails diversion of a portion of the process stream substantially directly to a chemical analysis device.

The term "at-line" herein refers to sample analysis of a process stream than entails diversion and collection of a portion of the process stream prior to analysis of the collected portion. Collection occurs either external to a particular analysis tool or internal to the tool. Collected portions are, for example, collected in sample vials. The terms in-line, on-line and at line are terms of convenience, and are not intended to be rigid; therefore, it will be understood that some overlap in these definitions may exist.

The word "chromatography" and the like herein refer to equipment and/or methods used to perform separation of chemical compounds. Chromatographic equipment typically moves fluids under pressure and/or electrical forces. The acronym "HPLC" (high-pressure or high-performance LC) is used herein generally to refer to liquid chromatography performed at pressures of approximately 1,000 to 2,000 psi or greater. "UHPLC" (ultra high-pressure or ultra-high-performance LC) is used herein generally to refer to liquid chromatography performed at pressures of up to approximately 15,000 to 20,000 psi or greater.

The term "sample loop" is used herein to refer broadly to any suitable container, vessel, conduit, or tube that temporarily holds a sample portion prior to injection and separation, including, for example, sample loops that are known to one having ordinary skill in HPLC and UHPLC.

The word "column" herein refers to a vessel, including, for example, one or more tubes, within which separation of compounds occurs.

Preferred embodiments of the invention entail methods and apparatus that interface UHPLC components to multiple sample sources. The methods and apparatus are suited, for example, to support of PAT initiatives for monitoring and/or control of drug-manufacturing processes. The embodiments described below support on-line and/or at-line analyses.

In some embodiments of the invention, an LC injection sequence is used to repeatedly and alternately sample flowing process streams and standards sources, through use of two multi-port valves and a syringe drive. One valve allows the selection of the desired stream or the desired associated standard while the second valve allows the introduction of the selected fluid into the LC stream of an analyzer.

Figure 1:
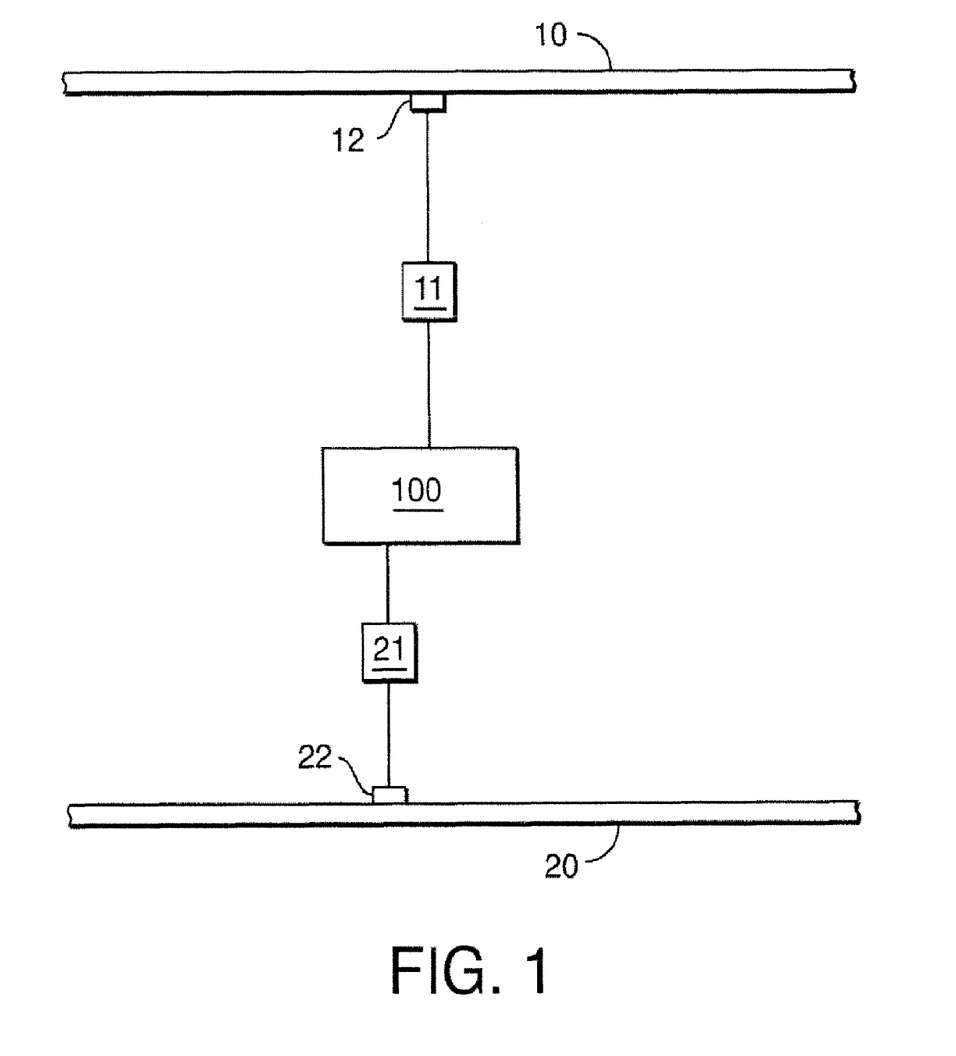
FIG. 1 is a block diagram of a PAT tool and associated process lines supported by the PAT tool, in accordance with one embodiment of the invention.

FIG. 1 is a block diagram of an analytical apparatus 100 for monitoring multiple process streams in pharmaceutical manufacturing; the diagram also illustrates portions of process lines 10, 20 (e.g., plumbing such as tubes) carrying different process streams. The process lines 10, 20 have associated ports 12, 22 to support diversion of portions of the associated process streams. Each port 12, 22 is plumbed to a respective valve 11, 21. The valves 11, 21, in turn support interfacing to the apparatus 100 via additional plumbing.

Plumbing, ports and valves, in various embodiments of the invention, are any suitable components, including components known to one of ordinary skill in the LC arts. One of ordinary skill will understand that it is desirable to minimize the quantity of diverted material and the flow-path distance from a process line to an analyzer portion of an apparatus.

The apparatus 100 is optionally configured for on-line and/or for at-line analyses. For at-line support, the apparatus 100 includes components that collect samples and components that transport the collected samples to an analyzer portion of the apparatus 100. The analyzer portion preferably provides relatively high-speed analyses in support of the rapid response desired in a typical pharmaceutical manufacturing setting. The apparatus 100 is optionally a modified version of an ACQUITY UPLC® chromatography apparatus (available from Waters Corporation, Milford, Mass.)

Next, an example of an apparatus and its operation are described in more detail. FIGS. 2a through 2e are schematic diagrams of a portion of an analytical apparatus 200, in accordance with one embodiment of the invention; the diagrams illustrate an example of operation of the apparatus 200, as described in more detail below. The apparatus 200 includes an injection valve 210, a selection valve 220, a sample pump 230, three sources 240 that each contain a different standard solution, and various tubing lines L1-L8 that support plumbing to fluidically connect the various components of the apparatus 200.

Figure 2A:
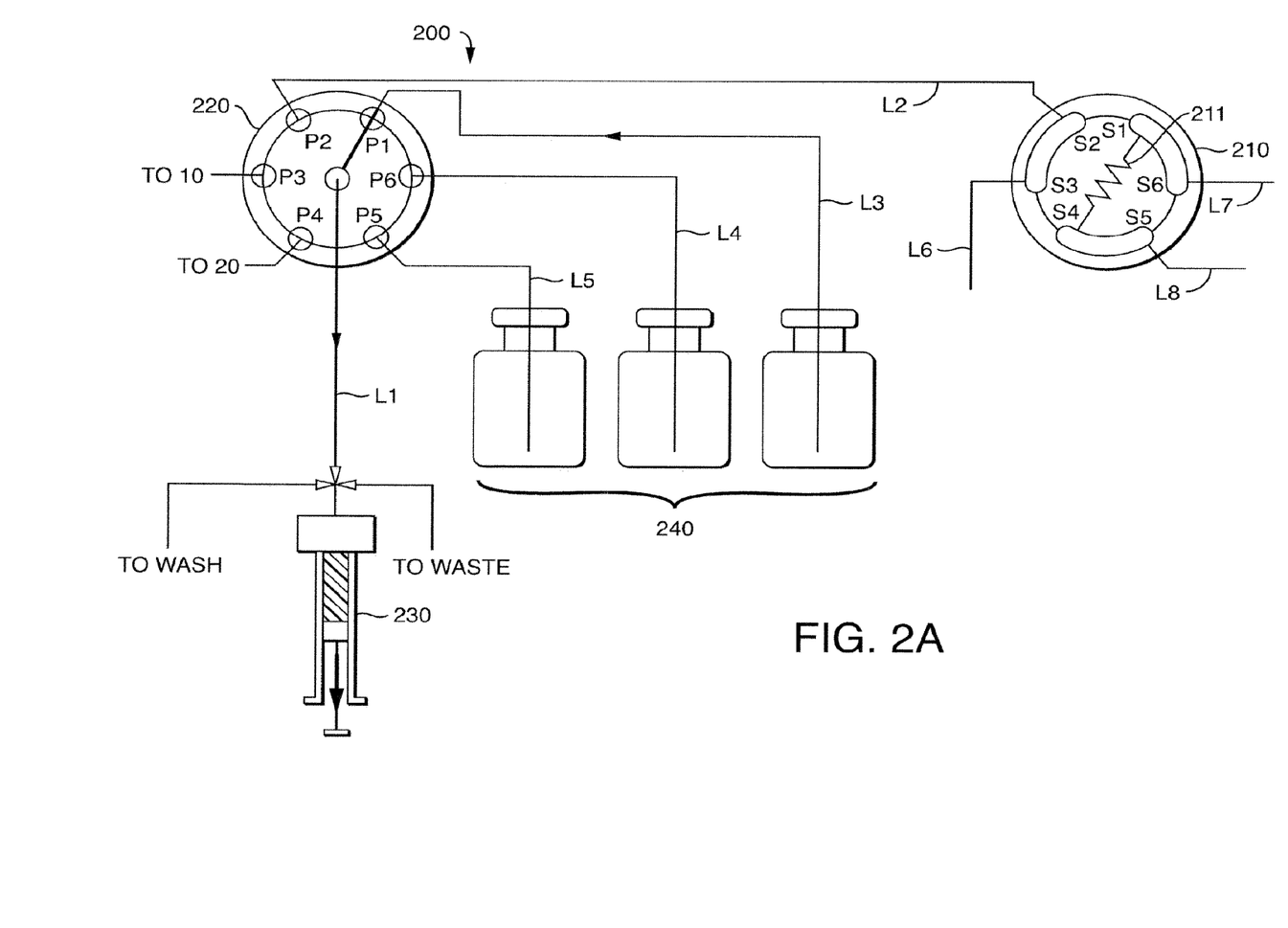
FIG. 2a is a diagram of portion of a PAT tool, in accordance with one embodiment of the invention, illustrating a draw state.

The selection valve 220 has six ports P1-P6 on its perimeter and a seventh, central port P7. The central port P7 is a common inlet/outlet port that is switchably connected to the other six ports P1-P6. The central port P7 is plumbed to the sample pump 230 via a tube L1, while three of the peripheral ports P1, P5, P6 are plumbed to the standards sources 240 via tubes L3, L4, L5 and one port P2 is plumbed to the injection valve 210 via a tube L2. The two remaining ports P3, P4 of the selection valve 220 are interfaced to two different process lines, such as being plumbed to the valves 11, 21 shown in FIG. 1. The lines L1-L8 are any suitable tubing, such as tubing know in the chromatography arts, such as stainless steel tubing or fused-silica capillary tubing.

The selection valve 220 switchably connects the pump 230 to one of the process streams 10, 20, the standards sources 240, or the injection valve 210. The valve 220 is optionally any suitable valve, including known selection valves. As illustrated, the valve 220 is a 6-position 7-port selection valve (available, for example, from Rheodyne LLC, IDEX Health & Science, Rohnert Park, Calif.) Thus, for example, the input ports P3, P4 receive drug-manufacturing-process fluid diverted from two process lines, such as the two lines 10, 20 shown in FIG. 1.

The sample pump 230 is selected from any suitable pumping device, including a known device, such as a chromatographic metering syringe. In this example embodiment, as indicated above, the sample pump 230 is fluidically connected via the tube L1 to the selection valve 220 at the central port P7.

The tube L1 optionally is kept to a minimum length to help reduce the time lag associated with transfer of a sample from one of the ports 11, 21 to the injection valve 210. Preferably, reliance on pulling of a sample is minimized while pushing of the sample is preferred. When pulling a sample, air pressure and tubing diameter are associated with a limit on flow rate; in effect, a vacuum pulls the sample, and is limited to ambient pressure, e.g., 14.7 psi. When pushing a sample, the pump 230 is able to apply much higher pressures, causing much higher flow rates.

The injection valve 210 has a sample loop 211 that receives the sample for loading into an analysis stream for delivery to a separation column (not shown,) as understood by one having ordinary skill in LC. Two tubes L7, L8 connect the process stream to the injection valve via two ports S5, S6. One tube L8 carries a mobile phase, such as a solvent, to the injection valve 210; after injection of a sample from the loop 211 into the mobile phase, the mobile phase and sample are delivered to the separation column via the other tube L7. The injection valve 210 includes, for example, any multiport valve that is suitable for switchably connecting conduits in a chromatographic system.

The apparatus 200 is optionally implemented as a HPLC or UHPLC system. In these cases, the injection valve 210 is any suitable valve, including any suitable commercially available injection valve that supports sample loading and/or injection in a HPLC or UHPLC system. For example, the injection valve 210 is optionally a 6- or 10-port loop injection valve (available, for example, from Bio-Chem Valve/Omnifit, Booton, N.J.)

The sample loop 211 is any suitable sample-holding component, such as a sample loop known to one having ordinary skill in chromatography. For example, the sample loop 211 has any desired volume, for example, a fixed volume of 2, 5, 10, or 20 µl, or more, such as 250 µl.

In the illustrated example, the injection valve 210 is a six-port injection valve. One port P2 of the selection valve 220, as noted, is plumbed to one of the ports S2 of the injection valve 210 via the tube L2. Two ports S1, S4 are plumbed to either end of the sample loop, two ports S5, S6 are plumbed to the fluidic pathway leading to the separation column, and the final port S4 is plumbed to a waste line.

Next, an example of operation of the apparatus 200 is described. First, one may note that the injection valve 210 is switchable between two configurations, to support the various steps involved in a typical LC analysis, such as: drawing a sample from a sample source; pre-loading the sample for delivery to a sample loop; loading the sample into the sample loop: injection of the sample from the sample loop into an analytical stream for separation; and washing of components, such as valves and tubes, as will be understood by one of ordinary skill in the LC arts. Such operations are selectable by appropriate selection of the states of the selection valve 220 and the injection valve 210. The selection valve 220 is switchable between six configurations or states, each position permitting the pump 230 to push and/or pull on any of the lines plumbed to the ports P1-P6; the injection valve 210 is switchable between two states.

In this example, one of the standard solutions, from the sources 240, is to be sampled. First, FIG. 2a illustrates a draw operation. The selection valve 220 is switched to a position that connects the desired one of the standard sources 240 to the pump 230 via the tube L3. The pump 230 draws a sample through the selection valve 220 and into the tube L1 that connects the pump 230 to the selection valve 220.

Figure 2B:
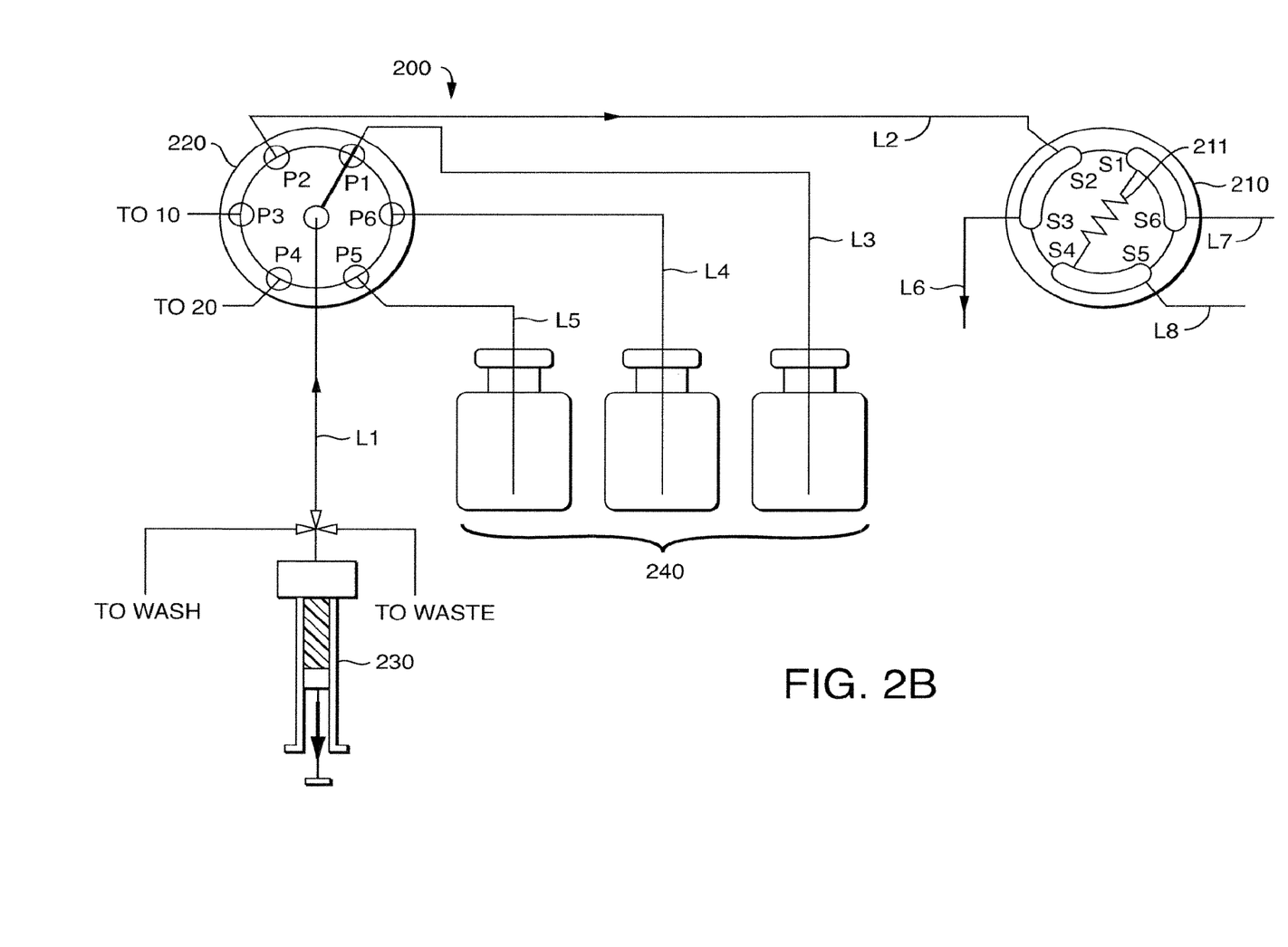
FIG. 2b is a diagram of the tool of FIG. 2a, illustrating a pre-load state.

Next, FIG. 2b illustrates a pre-load operation. The selection valve 220 is switched to connect the pump 230 to the injection valve 210, which in turn is switched to a state that supports pre-loading, in which the tube L2 is connected through the valve 210 to the tube L6 (i.e., waste.) The pump 230 pushes the drawn sample of standard back through the selection valve 220 to a position in the tube L2 adjacent to the injection valve 210 at port S2 or in the tube L6 adjacent to port S3.

Figure 2C:
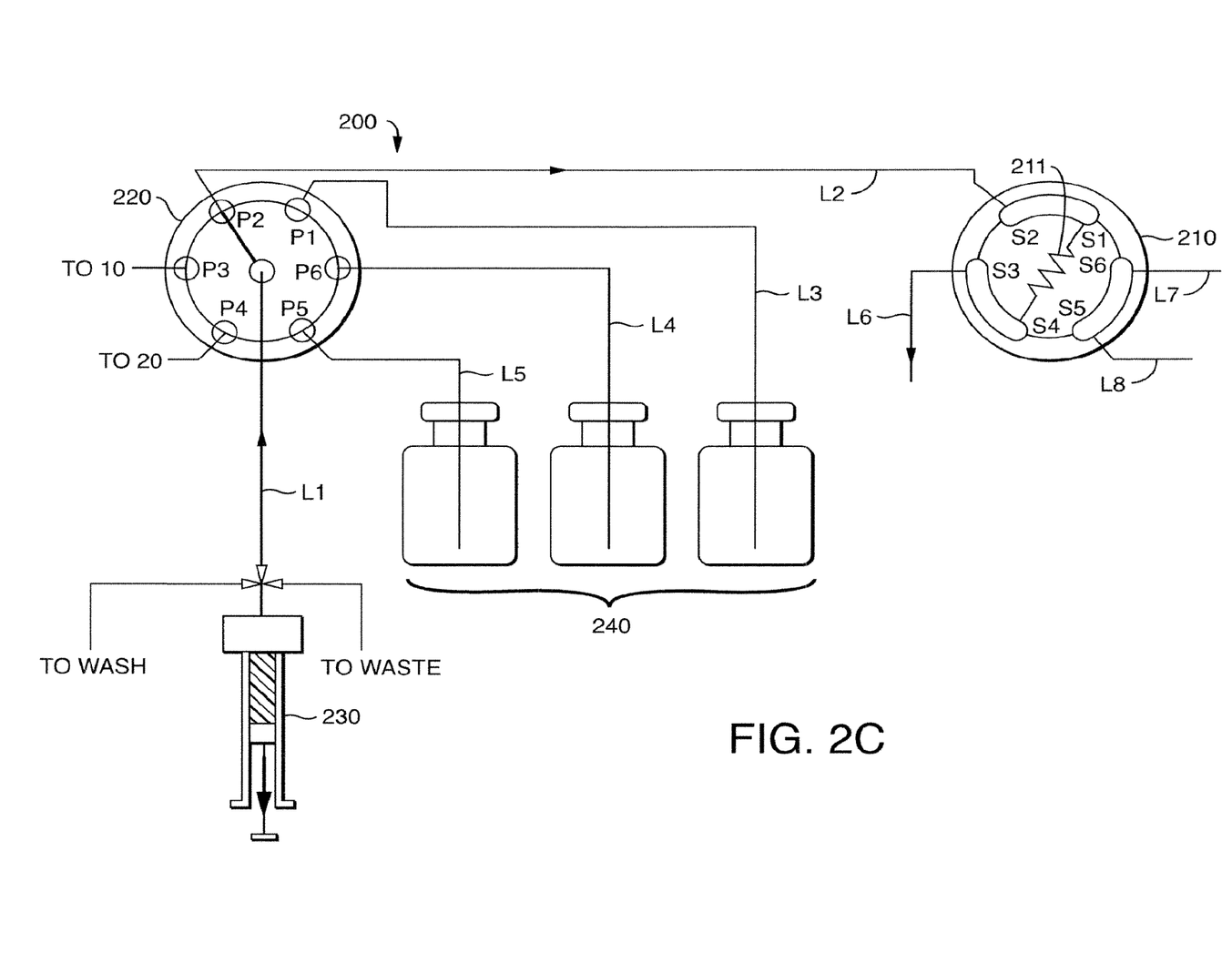
FIG. 2c is a diagram of the tool of FIG. 2a, illustrating a load state.

FIG. 2c illustrates a load operation. The injection valve 230 is switched to connect the pump 230 to the sample loop 211 via the injection valve 230 ports S1, S2. The pump 230 pushes, or pulls, the pre-loaded sample of standard onto the sample loop 211 respectively via the port S1 or the port S4.

Figure 2D:
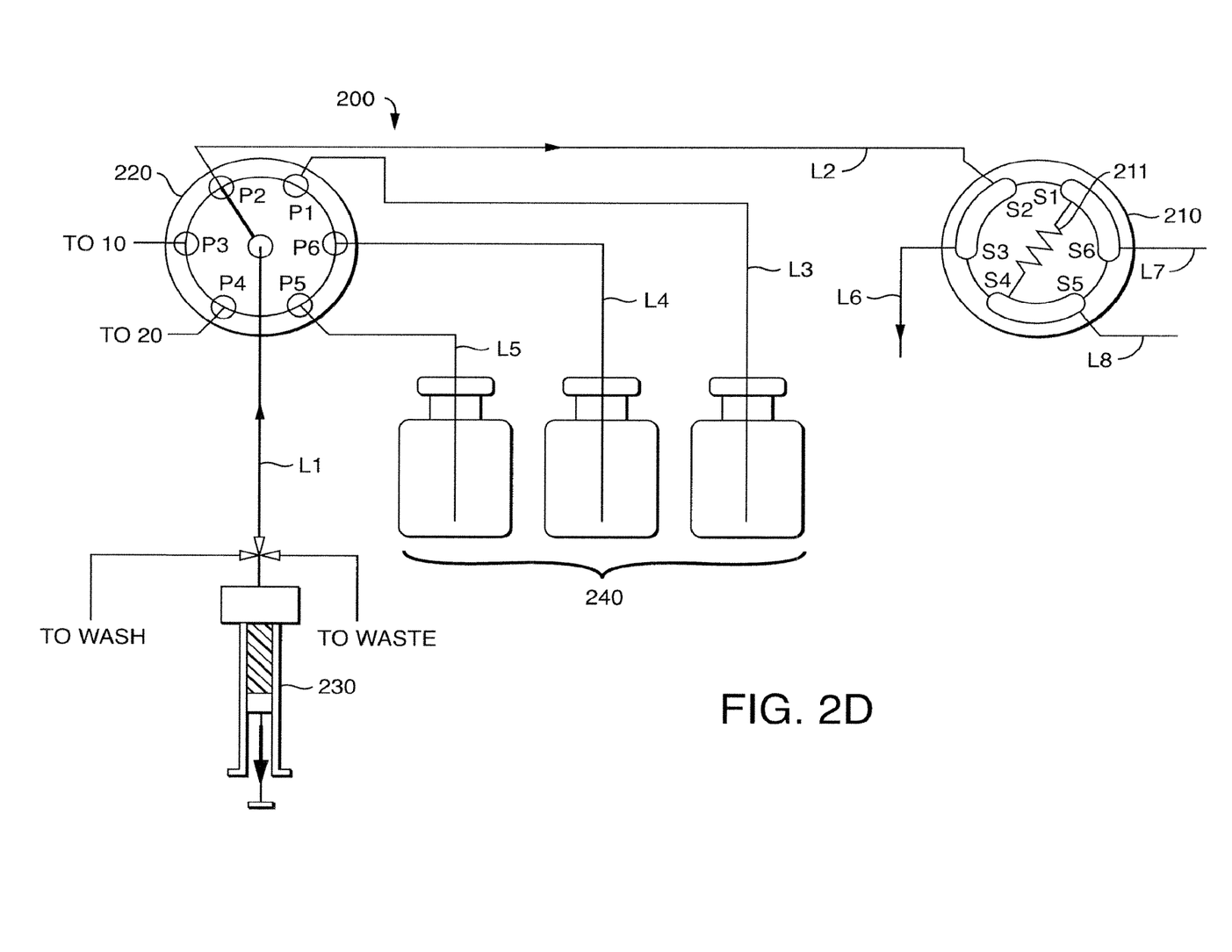
FIG. 2d is a diagram of the tool of FIG. 2a, illustrating an inject state.

FIG. 2d illustrates an injection operation. The injection valve 230 is switched to connect the sample loop 211 to the chromatography process stream, i.e., via the process-stream tubes L7, L8, so that the standard sample is delivered to the separation column for analysis.

Figure 2E:
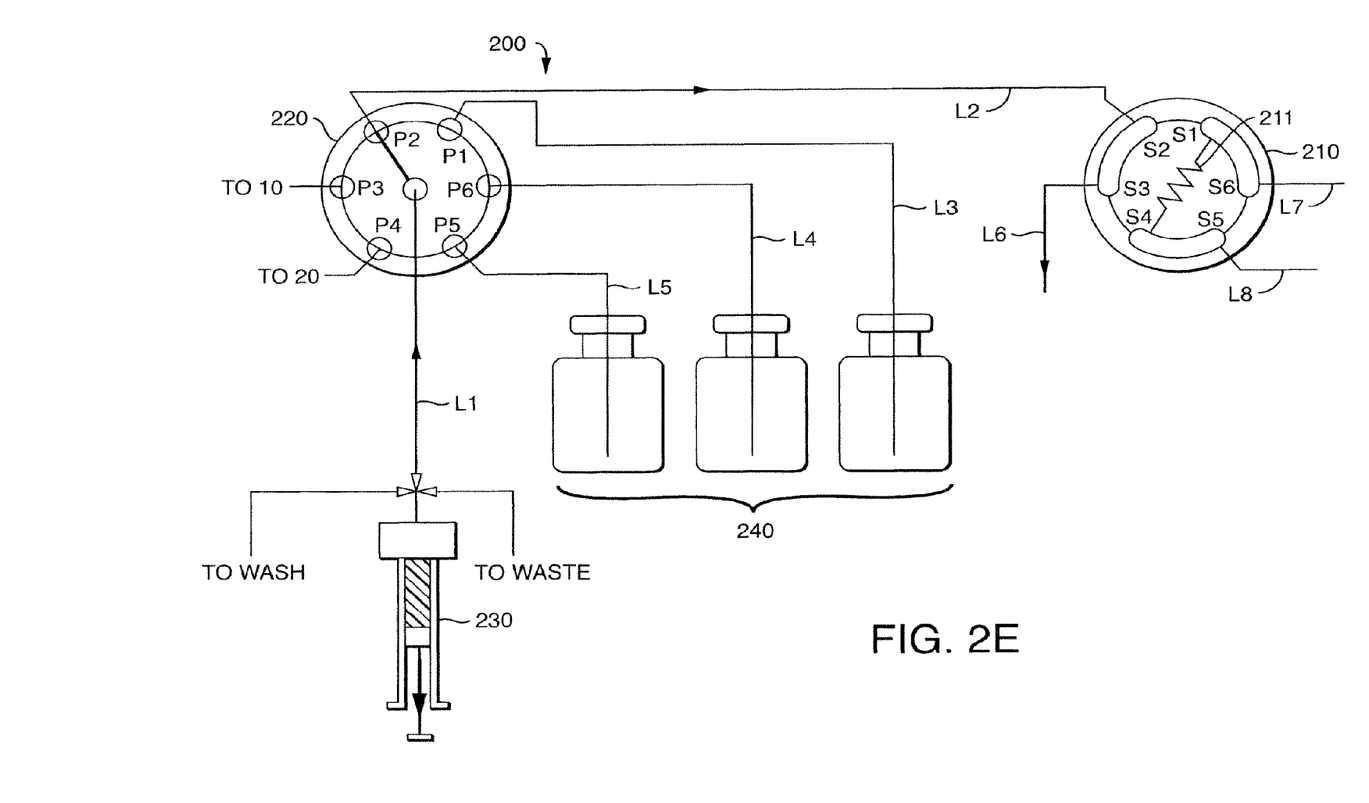
FIG. 2e is a diagram of the tool of FIG. 2a, illustrating a wash state.

Last, FIG. 2e illustrates a wash operation. A wash solution is drawn into the pump 230, and the pump 230 then pushes the wash solution through the injection valve 210 to the waste tube L6. The plumbing of the apparatus 200 is thus prepared for the next sample.

In a manner similar to that just described, the other standards sources 240 and the process lines 10, 20 are sampled, via appropriate selection by the selection valve 220. Repeated, alternating sampling of the multiple processes and multiple standards provides enhanced efficiency of pharmaceutical production.

The above examples have shown sample collection from manufacturing process lines via on-line connections. Alternative embodiments of the invention utilize at-line sample collection. As will be understood by one of ordinary skill in the LC arts, the apparatus is optionally configured to include collect process samples in, for example, vials; samples are then extracted from the vials for analysis.

Various embodiments of the invention are configured and operated to provide increased efficiency in pharmaceutical manufacturing. These embodiments preferably include all or some of the following features: quick sampling of multiple manufacturing process streams, sampling of multiple standard sources, rapid LC analyses, and repeated frequent analyses of the sampled process streams and the standards. Desirably, an LC analysis portion of such embodiments utilizes UHPLC. Such an analysis portion performs a sample analysis in, for example, minutes rather than, for example, the half hour to an hour required by some prior systems.

With the above features, an apparatus can monitor the manufacturing processes in close to a real-time manner and can collect data points spaced closely in time, for example, spaced by minutes or tens of minutes rather than by a half hour to an hour or more. Once a desired drug product begins to appear in a process stream, collection of the drug can commence with relatively accurate identification of the location of the drug in the stream. Similarly, the end of a product run is identified to permit accurate termination of collection. These features reduce the burden of holding the process stream in plumbing connections and tracking the location of the process stream as it proceeds while data analysis proceeds with delay.

Thus, substantial efficiency gains are obtainable through use of a single apparatus—located on a manufacturing floor—that supports multiple process streams, provides rapid repeated analyses of the multiple manufacturing processes, with rapid alternating repeated analyses of related standards. Due to the high costs involved in many drug manufacturing processes, such efficiency gains can provide substantial cost savings and increased product collection from each production batch.

Repeated, frequent monitoring of the performance of the apparatus through use of the standards not only provides repeated calibration data, but also provides fault detection of errors arising for example, do to a failure in the LC portions of the apparatus. It is desirable to detect such failures as soon as possible after the failure occurs (preferably immediately) to minimize any disruption in the manufacturing process and consequent costs. Monitoring is accomplished, for example, by confirming that standard analyses fall within a constant tolerance window or fall with a selected window relative to a prior measurement.

The standards sources 240 contain any solutions, as desired, to support analysis of manufacturing processes and apparatus monitoring. For example, the standards optionally have varying concentrations and/or varying compositions of desired materials. The materials optionally are associated with particular materials under manufacturing.

The apparatus 200 optionally includes a control unit that mediates its operation. The control unit—including, for example, a personal computer or workstation—exchanges data and/or control signals via wired and/or wireless communications with, for example, the injection valve 210, the selection valve 220, and/or the pump 230. The control unit supports, for example, automation of sample analyses. The control unit, in various alternative embodiments, includes software, firmware, and/or hardware (e.g., such as an application-specific integrated circuit), and includes, if desired, a user interface. The control unit is optionally configured to implement the above-described sampling and monitoring processes described above.

In view of the description provided herein, one having ordinary skill in the chromatographic arts will recognize that various embodiments of the invention are not limited to specific features described above. Variations, modifications, and other implementations of what is described herein will occur to those of ordinary skill in the art without departing from the scope of the invention as claimed. Accordingly, the invention is to be defined not by the preceding illustrative description but instead by the following claims.

What is claimed is:

1. An analytical apparatus, comprising:
    a injection valve comprising a sample loop, and having an output port in fluid communication with a liquid chromatography column and an input port in fluid communication with a mobile-phase supply line;
    a sample pump;
    at least two sources of standards associated with at least two pharmaceutical compounds; and
    a selection valve that fluidically and selectably connects the sample pump to one of the at least two sources of standards, to the injection valve, or to one of at least two pharmaceutical manufacturing process lines associated with the at least two pharmaceutical compounds.

2. The apparatus of claim 1, wherein the sample pump comprises a syringe.

3. The apparatus of claim 1, wherein the injection valve further comprises a six-port valve.

4. The apparatus of claim 1, wherein the selection valve comprises a seven-port selection valve.

5. The apparatus of claim 1, wherein the at least two sources of standards have different concentrations of a solution.

6. The apparatus of claim 1, wherein the at least two sources of standards each comprise one of the at least two pharmaceutical compounds.

7. The apparatus of claim 1, further comprising means for controlling the injection valve, the selection valve and the sample pump.

8. The apparatus of claim 7, further comprising means for detecting a fault in an LC portion of the apparatus.

9. A method for controlling a pharmaceutical manufacturing process, comprising:
    providing an apparatus comprising
        a sample-injection valve comprising a sample loop, and having an output port in fluid communication with a liquid chromatography column and an input port in fluid communication with a mobile-phase supply line,
        a sample pump,
        at least two sources of standards associated with at least two pharmaceutical compounds, and
        a selection valve that fluidically and selectably connects the sample pump to one of the at least two sources of standards, to the injection valve, or to one of at least two pharmaceutical manufacturing process lines associated with the at least two pharmaceutical compounds; and
    switching the selection valve to alternately and repeatedly sample the at least two sources of standards and material flowing through the at least two pharmaceutical manufacturing process lines.

* * * * *